United States Patent [19]

Walters

[11] 4,180,069

[45] Dec. 25, 1979

[54] PLUNGER ROD AND PISTON FOR A SYRINGE

[75] Inventor: Ralph Walters, Perkiomenville, Pa.

[73] Assignee: The West Company, Phoenixville, Pa.

[21] Appl. No.: 782,562

[22] Filed: Mar. 29, 1977

Related U.S. Application Data

[63] Continuation of Ser. No. 691,902, Jun. 1, 1976, abandoned.

[51] Int. Cl.² ........................................... A61M 5/315
[52] U.S. Cl. ................................. 128/218 P; 128/234
[58] Field of Search ......... 128/218 P, 218 PA, 218 R, 128/220, 219, 234, 215, 221; 92/172, 209, 216, 228; 222/386, 386.5; 401/171-182

[56] References Cited

U.S. PATENT DOCUMENTS

| 2,473,733 | 6/1949 | Smith | 128/218 P |
| 2,495,027 | 1/1950 | Smith | 128/220 |
| 3,098,482 | 7/1963 | O'Sullivan | 128/220 |
| 3,831,601 | 8/1974 | Kessell | 128/219 |

FOREIGN PATENT DOCUMENTS

| 6400092 | 11/1965 | Netherlands | 128/234 |
| 315980 | 3/1969 | Sweden | 128/218 PA |
| 741604 | 12/1955 | United Kingdom | 128/218 D |

*Primary Examiner*—John D. Yasko
*Attorney, Agent, or Firm*—Eugene E. Renz, Jr.

[57] ABSTRACT

A plunger rod and piston for a syringe which are easily and quickly assembled with a minimum force. The plunger rod has a tip of truncated "christmas tree" shape and the piston, which is of a flexible resilient material, has a pocket of complementary shape to receive the plunger tip. The tip includes a series of frusto conical segments of decreasing cross-wise dimension from the base to the terminal end of the tip thereby defining a plurality of circumferentially extending, axially spaced radially directed shoulders.

The piston pocket has a series of frusto conical pocket sections decreasing in size from the open end thereof to define a plurality of circumferentially extending axially spaced, radially directed, flexible lips. Upon assembly of the tip in the piston pocket, the lips deflect to permit seating of the tip therein and then engage behind the radial shoulders to lock the parts together.

10 Claims, 8 Drawing Figures

PLUNGER ROD AND PISTON FOR A SYRINGE

This application is a continuation of my prior application Ser. No. 691,902 entitled PLUNGER ROD AND PISTON FOR A SYRINGE filed June 1, 1976 now abandoned.

BACKGROUND OF THE INVENTION

The present invention relates broadly to syringe assemblies and more specifically to a plunger rod and piston having novel locking means facilitating assembly easily and quickly with a minimum application force.

Typical syringe assemblies of the type to which the present invention relates include a piston or plunger which fits snugly in the barrel of the syringe and is adapted for actuation axially therein to aspirate and discharge contents through the hypodermic needle by means of a plunger rod attached to the piston. The piston and rod are separate elements having a suitable form of means for locking the parts together so they function as an integral unit.

Typical prior art techniques for attaching the plunger rod and piston are shown in U.S. Pat. Nos. 3,291,128, issued Dec. 13, 1966; 2,895,773 issued July 21, 1959 and 3,164,303 issued Jan. 5, 1965.

In U.S. Pat. No. 3,291,128, the plunger rod has a cylindrical tip with a plurality of radially extending, circumferentially spaced lugs and the piston has a pocket of an interior configuration corresponding to the plunger tip. The opening to the pocket is of a diametral dimension of substantially the same size as the cylindrical tip. Thus, a substantial force is required to press the tip in place since the lugs must be forced through a relatively thick walled narrow throat area of the piston. Furthermore, the parts have to be concentrically aligned before assembly and thus assembly by automatic equipment is practically impossible. The principal form of plunger rod and piston of U.S. Pat. No. 2,895,773 is basically the same as that described above. In addition, there are shown expansion lock arrangements which require post assembly manipulation to lock the parts together. U.S. Pat. No. 3,164,303 shows a screw threaded arrangement.

In syringe assemblies where the plunger and piston rod are assembled by the manufacturer, it has been found that the units mentioned above are only capable of being assembled by hand and do not lend themselves to faster, automated machine assembly techniques. In disposable syringes, the plunger is generally inserted into the barrel and the plunger rod maintained as a separate element until it is desired to activate the syringe. In disposable syringe assemblies, the forward end of the barrel usually has some form of diaphragm means or a cap closing the discharge end of the barrel. Presently in most of these disposable syringes, the plunger rod and piston are assembled by hand, which of course is time consuming and increases the cost of the overall assembly. These disposable syringe assemblies are usually housed in a somewhat flexible and pliable plastic package. This package is more elongated than if the plunger rod were included in the package as a separate item, and then assembled by the user when it is desired to use the syringe and this adds to the cost of manufacturing and shipping. Moreover there is also the danger of accidentally moving the plunger rod axially during packaging the assembly or in shipment which may prematurely rupture the diaphragm or displace the closure cap at the discharge end of the barrel. In some instances, the plunger rod is a separable element and in preparing the syringe for use, the user assembles the plunger rod to the piston, removes the closure cap and applies the needle to the end of the barrel. Some difficulties have been encountered in assembling the plunger rod by reason of the large axial force needed to seat the plunger rod in the piston in these prior assemblies. In some cases the force needed to assemble has been so great as to either burst the diaphragm prematurely or to create a sufficient internal pressure to blow the closure cap off the end of the barrel.

Accordingly, it is an object of the present invention to provide a new and useful plunger rod and piston including a novel locking arrangement facilitating assembly manually or by automatic machine techniques.

It is also an object of the invention to provide such an assembly wherein the parts assemble easily with a minimum force by a snap action and wherein the rod and piston are firmly secured together.

Another object is to provide such an assembly which is simple and inexpensive.

SUMMARY OF THE INVENTION

These and other objects of the present invention are achieved by the provision of a plunger rod having a tip portion of truncated "christmas tree" shape and a piston having a complementary shaped pocket therein. More specifically, the plunger rod tip comprises a series of frusto-conical segments of progressively descreasing cross-wise dimension from the base to the outer terminal end of the tip. The pocket in the piston likewise is of truncated "christmas tree" cross section converging inwardly from its open end toward the base in a series of tiered frusto conical pocket sections. The array of pocket sections define a plurality of axially spaced, flexible circumferential lips which deflect upon entry of the tip portion and then engage behind a radial shoulder of the frusto conical tip segments to lock the plunger rod in place. In the preferred arrangement, the frusto conical wall surface of the outer terminal tip segment of the plunger rod has a wider angle of taper than its complementary pocket section whereas the othertip segments and complementary pocket sections have a reverse relationship. By this configuration, the plunger rod seats easily in the plunger with a comparatively small application force and yet locks firmly in place and resists disassembly which is a feature facilitating aspiration. Moreover, since the plunger rod tip is substantially smaller than the outer pocket section, critical alignment of the two for assembly is unnecessary. Accordingly, the piston and plunger rod are easy to assemble even by automatic equipment without any prealignment or post manipulation operations. The specific arrangement is, in effect, self-aligning. In an alternate embodiment, the piston has an enlarged cavity adjacent the lowermost frusto conical pocket portion. This cavity is of a depth defining a thin, flexible wall area at its outer end confronting the contents in the barrel of the syringe providing expansion capabilities without unseating the piston for certain medicaments which tend to expand during storage.

BRIEF DESCRIPTION OF THE FIGURES

These and other objects and features of the invention will be more readily understood from a consideration of the following details, taken in connection with the accompanying drawings, in which.

DESCRIPTION OF SPECIFIC EMBODIMENTS

Figure 1:
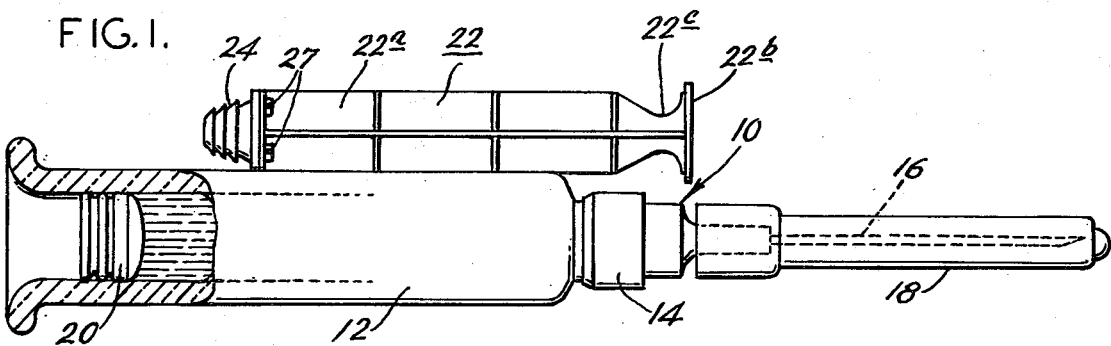
FIG. 1 is a side elevational view partly in section of a syringe assembly incorporating a plunger rod and piston assembly in accordance with the present invention, the plunger rod being shown prior to assembly to the piston.

Referring now to the drawing and particularly to FIG. 1 thereof, there is illustrated by way of example only, a typical syringe assembly generally designated by the numeral 10. The assembly includes an elongated hollow barrel 12 which may be made of glass having a needle hub 14 at its discharge end which supports over the discharge end of the barrel 12 a standard hypodermic needle 16 usually protected by a shield 18 prior to use. In some syringes, the needle hub supports a diaphragm over the discharge end of the barrel which either bursts or is displaced upon actuation of the piston forwardly to permit discharge of the contents. In other syringes, the hub, needle and shield are packaged as separate items and a removable closure cap placed over the hub at the discharge end of the barrel. When the syringe is readied for use the cap is removed and the needle attached to the barrel discharge end by the hub. The barrel contains a quantity of a medicament which is sealed therein by means of a piston 20. The piston 20 is usually made of an elastomeric material such as rubber and of a composition which will not react adversely with the medicament in the syringe barrel. The outer surface of the piston confronting the inner wall of the barrel 12 may be provided with one or more circumferentially extending axially spaced ribs 20a facilitating movement of the piston in the barrel. The syringe assembly further includes a plunger rod 22 having a tip 24 engageable in a pocket 26 in the piston. The plunger rod 22 which may be made of a semi-rigid plastic material such as polyproylene, comprises in the present instance an elongated ribbed stem 22a terminating at one end in a circular thumb piece to accomodate the index and forefinger of the user. In the illustrated form the tip 24 is attached to the stem by screw fasteners 27 although the unit may be one piece if desired. In the present instance, the plunger rod is a separate unit and is adapted for assembly to the piston at the time of using the syringe. In some instances the plunger rod and piston are assembled as a unit before insertion in the barrel. The locking arrangement of the present invention is also useful in these assemblies since the parts can be assembled quickly by automatic mass assembly equipment.

In accordance with the invention, the pocket 26 in the piston and the plunger rod tip are of a predetermined structural arrangement and configuration to facilitate assembly of the rod and piston with a minimum of effort, that is, by application of a small axial force which firmly locks the parts in place to permit movement of the two as a unit axially in the barrel of the syringe in both directions, rearwardly for aspiration and forwardly to discharge the contents of the barrel through the syringe needle. Minimization of the force required to assemble the plunger rod in the piston, of course, reduces the chance of displacing the piston forwardly prematurely which may in the case of some types of syringes cause premature rupture of the diaphragm and consequent loss of medicament product and in other cases, cause displacement of the protective cap over the discharge opening. The locking arrangement of the invention also facilitates complete assembly of the rod and piston by automatic equipment, without the need for precise alignment of the parts or any manual manipulation to permanently secure the parts together. The piston is conventionally made of a resilient elastomeric material such as natural or synthetic rubber, so that it snugly fits in the barrel and provides a seal and yet is capable of being easily moved axially in the barrel. To effect good sealing, the piston usually has a series of ribs formed on its outer periphery and the maximum plunger diameter is generally sized to provide an interference fit in the barrel. In this respect, the greatest piston diameter is about six percent larger than the barrel diameter.

Figure 3:
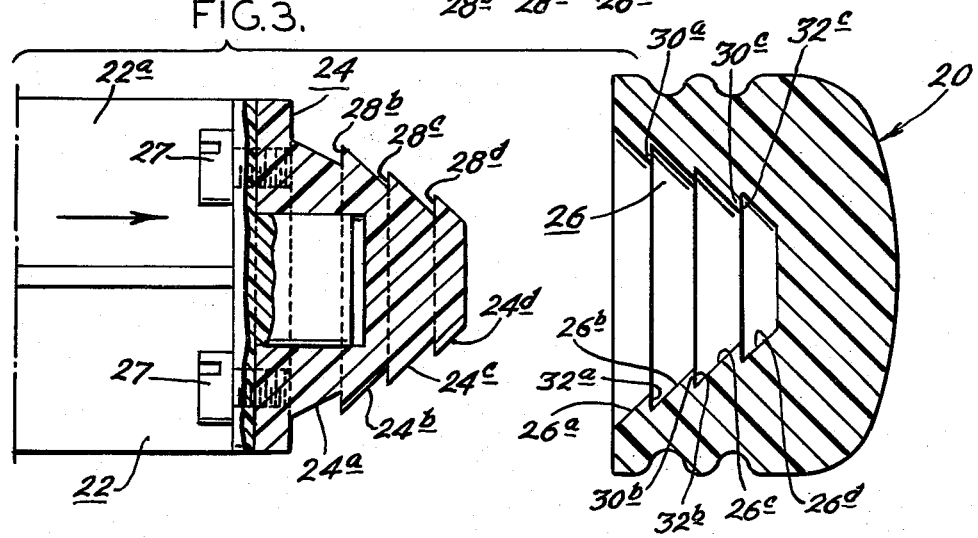
FIG. 3 is a view similar to FIG. 2 prior to assembly.
Figure 4:
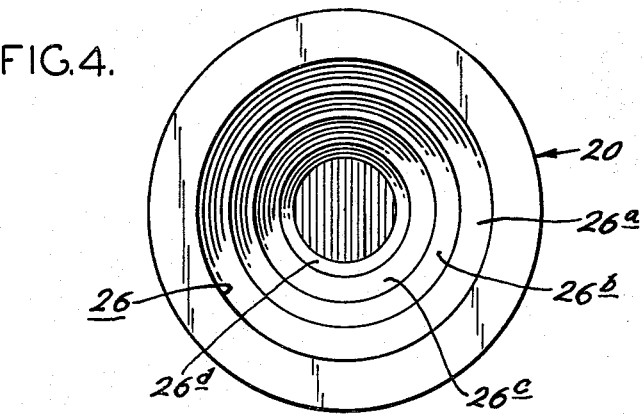
FIG. 4 is a top plan view looking into the open end of the piston.

In accordance with the invention, the plunger rod tip 24, as best illustrated in FIG. 3, is of truncated "christmas tree" shape comprising a series of frusto conical tip segments 24a, 24b, 24c and 24d of progressively decreasing size from the base of the tip to the outer terminal end thereof. The base of each segment 24b, 24c and 24d is of larger diameter than the top of the adjacent lower segment providing a series of axially spaced, circumferentially extending radially directed shoulders 28b, 28c and 28d.

Figure 2:
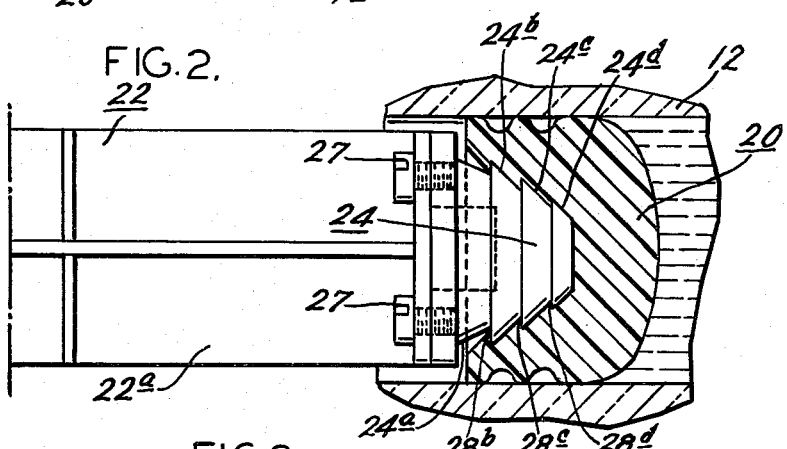
FIG. 2 is an enlarged fragmentary sectional view showing the plunger rod and piston in an assembled state.
Figure 5:
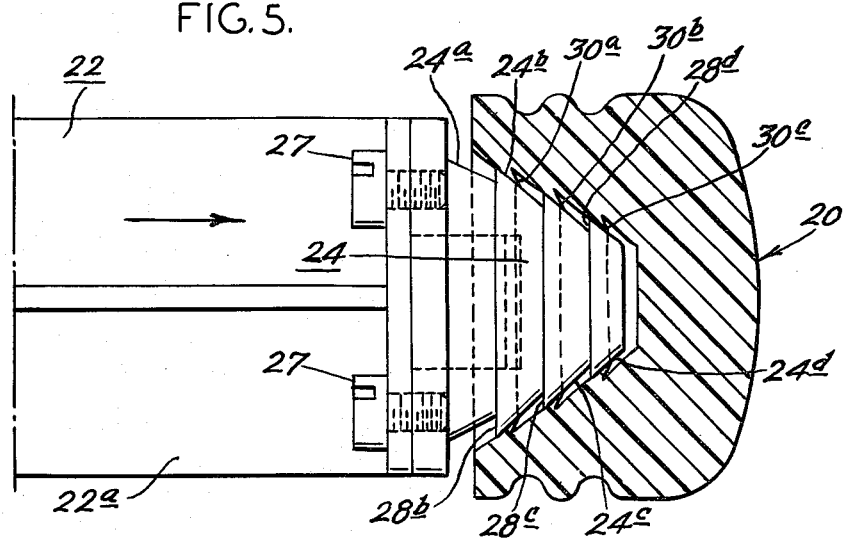
FIG. 5 is a view of the plunger rod and piston in a partially assembled state.

The pocket 26 in the piston is also of a truncated "christmas tree" shape in cross section complementing the configuration of the plunger rod tip to snugly embrace the same in the assembled relation. More specifically, the pocket 26 includes a series of frusto-conical shaped sections 26a, 26b, 26c and 26d decreasing in size from the open throat end of the piston. The pocket sections are concentric about a central axis and, as illustrated, the diameter of the base of each section is greater than the diameter of the inlet opening to the next adjacent section, thereby defining a series of axially spaced, circumferentially extending flexible ribs or lips 30a, 30b and 30c, each including a radially extending wall portion 32a, 32b and 32c respectively. These lips are flexed toward the bottom of the pocket when the tip of the plunger rod is inserted into the pocket (see FIG. 5) and when the piston rod has been fully seated, they engage behind the radial shoulder of each of the frusto conical tip sections of the plunger rod (see FIG. 2) and in this manner firmly secure the piston and plunger rod as a unit. It is noted that by reason of the sizing of the parts and the flexibility of the lips, only a small seating force is required to press the tip of the plunger rod to its seated position. In this manner, the danger of premature displacement of the piston is minimized, particularly important in the case of prefilled syringes where the piston is assembled in the barrel as a separate element. The complementary plunger rod and piston configuration also is easy to disassemble by a simple tilting of the plunger rod first to one side whereby the ribs on the tip are released from the flexible lips for a portion of their circumference. Then tilting the piston rod to the opposite side of the axis of the plunger releases the ribs completely, the rib portion initially released acting as a fulcrum on the displaced lips of the piston.

The low force, snap action assembly of the plunger rod and piston of the present invention is facilitated by the general arrangement of the tip of the plunger and the pocket in the piston as described above. In the preferred embodiment, however, there is a specific angular relationship of the frusto-conical tip sections in relation to one another and to the corresponding sections of the pocket in the plunger within which they seat in the locked position to provide the optimum assembly action. To this end the included taper angle of the tip segments decrease in size from the outer tip segment 24d to the tip segment 24a and the intermediate pocket sections 26b and 26c are tapered at a greater angle than the innermost and outermost sections 26a and 26d, the angle of taper A of pocket section 26d being greater than the angle E of section 26a. Further, the included taper angle A of the peripheral conical wall of the first pocket section 25d is preferably smaller than the included angle A' of the peripheral conical wall of the outermost frusto conical tip section 28d of the plunger rod and the taper angles B and C of the peripheral conical walls of the intermediate pocket sections are greater than the taper angles B' and C' respectively of the peripheral walls of the intermediate frusto conical tip sections 28b, 28c of the plunger rod. The peripheral conical wall of the outermost pocket section 26a is preferably tapered at a larger included angle E than the taper angle E' of the conical wall of base section 24a of the plunger tip. Further, the axial height $H_d$ of the frusto conical tip section 28d of the plunger rod is preferably about the same as, or slightly less than, the axial depth $H'_d$ of the lowermost pocket section 26d and the base and intermediate sections of the plunger tip are preferably of slightly greater axial height $H_a$, $H_b$ and $H_c$ than the depth $H'_a$, $H'_b$ and $H'_c$ of corresponding pocket sections in the plunger. The base diameter $D_a$, $D_b$, $D_c$ and $D_d$ of each of the tip sections is preferably slightly smaller than the base diameter $D'_a$, $D'_b$ $D'_c$ and $D'_d$ of its corresponding pocket section in the plunger. The top diameter $T_a$, $T_b$, $T_c$ and $T_d$ of each tip section is preferably smaller than the top diameter $T'_a$, $T'_b$, $T'_c$ and $T'_d$ of its corresponding plunger pocket section.

It has been found that these relationships provide for a tight fit once the plunger tip is assembled. Note that the slightly enlarged pocket sections 26b and 26c allow for reduction in size in these sections when the piston is inserted in the barrel with a press fit since the wall thickness of the piston is smaller adjacent its open end.

Listed below are two plunger rod piston assemblies in accordance with the present invention including the preferred size relationships generally set forth above.

EXAMPLE I
PLUNGER ROD

| TOP DIAMETER | BASE DIAMETER | AXIAL HEIGHT |
|---|---|---|
| $T_a = 0.575''$ | $D_a = 0.688''$ | $H_a = 0.130''$ |
| $T_b = 0.460''$ | $D_b = 0.660''$ | $H_b = 0.140''$ |
| $T_c = 0.350''$ | $D_c = 0.555''$ | $H_c = 0.130''$ |
| $T_d = 0.268''$ | $D_d = 0.440''$ | $H_d = 0.100''$ |

TAPER INCLUDED ANGLE

A = 45°
B = 80°
C = 88°
D = 90°

PISTON

| TOP DIAMETER | BASE DIAMETER | AXIAL HEIGHT |
|---|---|---|
| $T'_a = 0.640''$ | $D'_a = 0.750''$ | $H'_a = 0.100''$ |
| $T'_b = 0.515''$ | $D'_b = 0.735''$ | $H'_b = 0.125''$ |
| $T'_c = 0.390''$ | $D'_c = 0.610''$ | $H'_c = 0.125''$ |
| $T'_d = 0.280''$ | $D'_d = 0.485''$ | $H'_d = 0.100''$ |

TAPER INCLUDED ANGLE

A' = 60°
B' = 97°
C' = 97°
D' = 83°

EXAMPLE II
PLUNGER ROD

| TOP DIAMETER | BASE DIAMETER | AXIAL HEIGHT |
|---|---|---|
| $T_a = 0.150''$ | $D_a = 0.182''$ | $H_a = 0.075''$ |
| $T_b = 0.114''$ | $D_b = 0.182''$ | $H_b = 0.060''$ |
| $T_c = 0.076''$ | $D_c = 0.150''$ | $H_c = 0.060''$ |
| $T_d = 0.036''$ | $D_d = 0.110''$ | $H_d = 0.055''$ |

TAPER INCLUDED ANGLE

A = 25°
B = 59°
C = 62°
D = 67°

PISTON

| TOP DIAMETER | BASE DIAMETER | AXIAL HEIGHT |
|---|---|---|
| $T'_a = 0.160''$ | $D'_a = 0.197''$ | $H'_a = 0.060''$ |
| $T'_b = 0.120''$ | $D'_b = 0.196''$ | $H'_b = 0.060''$ |
| $T'_c = 0.080''$ | $D'_c = 0.156''$ | $H'_c = 0.060''$ |
| $T'_d = 0.036''$ | $D'_d = 0.114''$ | $H'_d = 0.060''$ |

TAPER INCLUDED ANGLE

| EXAMPLE II | | |
|---|---|---|
| PLUNGER ROD | | |
| TOP DIAMETER | BASE DIAMETER | AXIAL HEIGHT |
| A' = 40° | | |
| B' = 79° | | |
| C' = 79° | | |
| D' = 54° | | |

Figure 6:
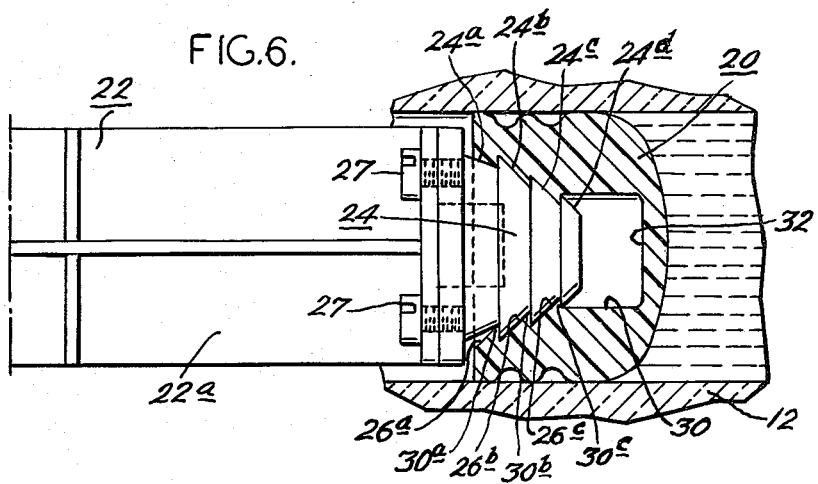
FIG. 6 is a transverse sectional view of a modified form of piston in accordance with the present invention.
Figure 7:
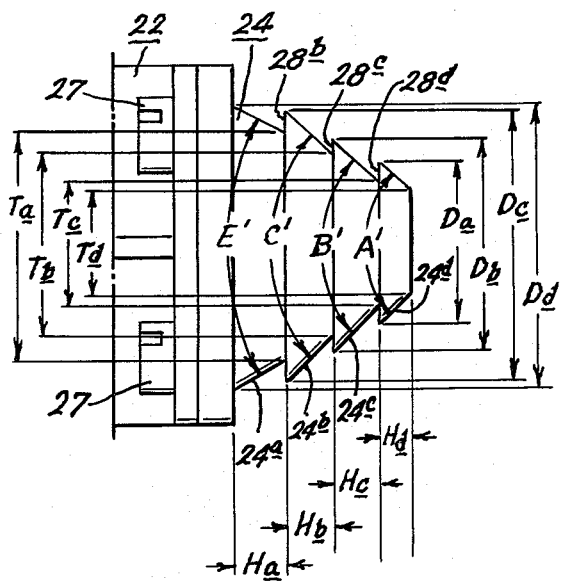
FIGS. 7 and 8 are side elevational and transverse sectional views of the plunger rod tip and piston.
Figure 8:
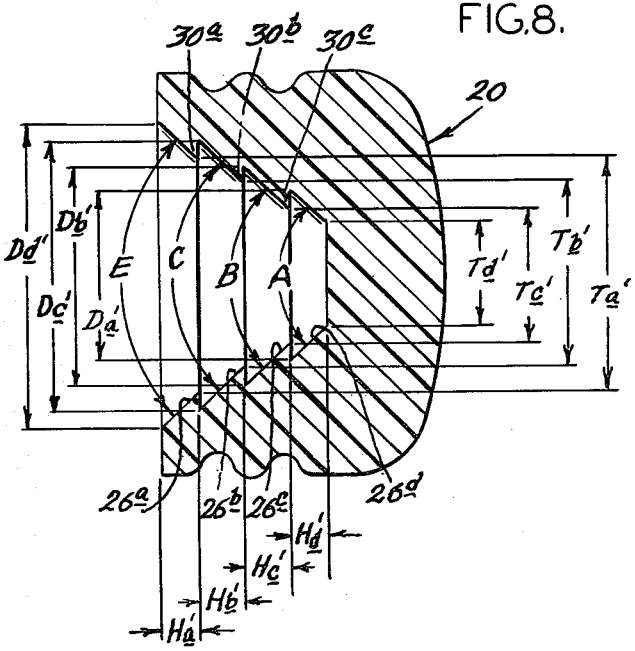

There is illustrated in FIG. 6 a plunger rod-piston assembly in accordance with the present invention. The plunger rod is of identical configuration to that described above and accordingly the same reference numerals to designate parts thereof have been used. The piston is basically the same except that in the present instance the innermost pocket section has been enlarged to define a cavity 30 extending to a predetermined depth to define a thin walled disc section 32 in the face of the piston. This thin walled section 32 is capable of inward deflection as shown in phantom lines and provides a means permitting expansion of the liquid product in the barrel without causing axial displacement of the piston. Certain products such as sodium bicarbonate tend to decompose and expand during storage and for given temperature variations.

In accordance with a method for designing the plunger rod tip and piston pocket to provide the desired snug fit in the assembled relation, the piston is assembled in the barrel and the pocket is then filled with a casting material such as silicone. A casting is then made from the silicone pattern. The plunger rod tips are then molded by conventional techniques. By this process it has been found that the plunger rod tip fills the entire piston pocket when assembled in a barrel to provide the desired snug fit therebetween.

Note that in the plunger rod-piston assemblies exemplified above, the outermost segment of the plunger rod tip is substantially smaller than the inlet pocket section of the piston. By this arrangement it can be seen that upon initial application of the plunger rod, for example, by automatic equipment, there is relatively large clearance between the tip and the pocket so that they do not have to be concentrically aligned in order to assemble. In this manner the parts are self centering thereby obviating the problems of some prior assemblies where the rod and piston must be absolutely concentric for assembly purposes. Once assembled the parts are securely locked together when the assembly is activated in an axial direction, which is the normal stroking movement for aspiration and injection since the shoulder of each tip segment firmly engages against the pocket section radial walls to resist separation. However, the parts may be easily disassembled if necessary by simply tilting or cocking the axis of the plunger rod relative to the axis of the plunger. By this movement the lips of the piston flex sufficiently to release from the tip of the piston rod about a portion of the circumference and then a cocking action in the opposite direction provides for full release very readily.

Thus, while the invention has been described with particular reference to specific embodiments thereof, it will be understood that it may be embodied in a variety of forms diverse from those specifically shown and described, without departing from the spirit and scope of the invention as defined by the appended claims.

I claim:

1. A plunger rod for a syringe assembly comprising an elongated stem and a tip at one end adapted to seat in a pocket in a piston, said tip being of generally truncated christmas tree shape and including a plurality of frusto-conical tip sections decreasing in cross wise dimension progressively from the base to the outer terminal end of the tip thereby defining a series of circumferentially extending axially spaced radially directed shoulders between adjacent tip sections, the included taper angle of the conical wall of the outermost tip section being greater than that of the remaining tip sections and the conical wall of the other tip sections decreasing progressively to the base of the tip.

2. A plunger rod as claimed in claim 1 wherein the axial height of the outermost tip section is smaller than the axial height of remaining tip sections.

3. A plunger rod as claimed in claim 1 wherein at least said tip is made of a semi-rigid plastic material such as polypropylene.

4. A piston made of a flexible material adapted to be assembled to a plunger rod and being of generally cylindrical shape, said piston having a pocket extending inwardly from one inner axial end face thereof, said pocket being of a truncated christmas tree configuration in cross section defining a series of pocket sections decreasing in cross wise dimension from the open throat end of the piston to define a series of circumferentially extending radially inwardly directed flexible lips between adjacent pocket sections, the conical wall of the innermost and outermost pocket sections being tapered at an included angle less than the angle of taper of the conical wall of the intermediate pocket sections.

5. A piston as claimed in claim 4 wherein the conical wall of the innermost pocket section remote from said one axial end face is tapered at an included angle greater than that of the outermost pocket section.

6. A piston as claimed in claim 4 made of an elastomeric material such as natural or synthetic rubber.

7. A piston as claimed in claim 4 wherein the pocket also includes a generally cylindrical cavity extending to a depth from the pocket to define a disc-like thin walled section at the outer axial end face of the piston.

8. The combination of a plunger rod, a piston adapted to be assembled to one another, and a barrel for a syringe having a maximum internal diameter slightly smaller than the maximum outer diameter of said piston, the plunger rod including a tip of truncated christmas tree shape defining a series of tip segments of varying cross wise dimension providing a circumferential shoulder separating adjacent tip segments and the piston including a pocket of a complementary truncated christmas tree shape defining a series of pocket sections including an entrance section and of varying cross wise dimension providing a flexible lip separating adjacent pocket sections, the outer terminal tip section having a cross wise dimension substantially less than the entrance pocket section, said tip segments and pocket sections being suitably dimensioned so that when the tip is seated in the pocket, the peripheral shoulder of each tip section engages behind the flexible lip of its complementary pocket section, the frusto-conical of the outer terminal tip segment of the plunger rod having a wider angle of taper than its complementary pocket section and said other tip sections and complementary pocket sections having a reverse relationship.

9. The combination as claimed in claim 8 wherein the conical wall of the outermost pocket section is tapered at a larger included angle than the taper of the conical wall of the base section of the plunger tip.

10. The combination as claimed in claim 8 wherein the axial height of the outermost tip section is substantially the same as the axial height of the innermost pocket section and wherein the base and intermediate tip sections are preferably of a slightly greater axial height than the depth of the corresponding pocket sections in the piston.

* * * * *